(12) United States Patent
Biernat, Jr. et al.

(10) Patent No.: US 6,572,686 B1
(45) Date of Patent: Jun. 3, 2003

(54) APPARATUS FOR CONDENSING AND COLLECTING HOT GASES

(75) Inventors: John L. Biernat, Jr., Scotia, NY (US); William J. Wlaschin, Rexford, NY (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 10/073,994

(22) Filed: Feb. 14, 2002

(51) Int. Cl.[7] .............................. B01D 8/00; G01N 1/22
(52) U.S. Cl. .................... 96/108; 96/413; 55/DIG. 15; 73/863.11; 73/864.51
(58) Field of Search ................... 96/108, 152, 413, 96/417; 55/DIG. 15; 73/863.11, 863.12, 863.21, 863.23, 864.51, 23.2; 62/600, 606

(56) References Cited

U.S. PATENT DOCUMENTS

| | | | | |
|---|---|---|---|---|
| 3,712,074 A | * | 1/1973 | Boissin | 62/55.5 |
| 4,488,887 A | * | 12/1984 | Angel et al. | 55/308 |
| 4,584,887 A | * | 4/1986 | Galen | 73/863.31 |
| 5,301,536 A | * | 4/1994 | Ortega et al. | 73/31.07 |
| 5,617,727 A | * | 4/1997 | Zito | 62/55.5 |
| 6,196,050 B1 | * | 3/2001 | Ikeda et al. | 73/23.2 |

FOREIGN PATENT DOCUMENTS

JP     58-83287 A   *   5/1983

* cited by examiner

Primary Examiner—David A. Simmons
Assistant Examiner—Frank M. Lawrence
(74) Attorney, Agent, or Firm—Julia Cook Moody; Paul A. Gottlieb

(57) ABSTRACT

This invention collects and analyzes condensable gases using a cryogenic cooling device connected to a charcoal cold trap assembly. More particularly, it uses a removable cryogenic cooling device instead of liquid nitrogen to trap condensable gases. The invention has four major components: (1) a removable cryogenic cooling device (2) a vacuum canister, (3) a cold trap canister filled with activated charcoal, and (4) a cover assembly with welded inlet/outlet tubes and an o-ring seal between the cover assembly and the vacuum canister.

18 Claims, 5 Drawing Sheets

APPARATUS FOR CONDENSING AND COLLECTING HOT GASES

BACKGROUND OF THE INVENTION

1. Field of the Invention

This invention collects and analyzes condensable gases using a cryogenic cooling device connected with a charcoal cold trap assembly. More particularly, it uses a removable cryogenic cooling device instead of liquid nitrogen to trap condensable gases.

2. Background and Description of Related Art

When irradiated fuel samples are annealed at high temperatures, it is necessary to obtain a quantitative evaluation of the radioactive fission gas that is released. A cold trap can be used to condense, collect, and analyze this gas, in which the hot gas is transported from the high temperature area by a carrier or purge gas to a cold trap assembly filled with a high-surface-area substance, preferably activated charcoal. In the prior art, the cold trap is cooled with liquid nitrogen. The cooled charcoal condenses and "traps" the hot, radioactive gas. A radiation detector, in close proximity to the trap monitors when and how much radioactive condensable gas has been trapped. A thermocouple may be used to monitor the temperature of the hot gases. A radiation source may be used to calibrate the radiation detector. A vacuum canister insulates the cold trap. After analyses are complete, the charcoal then must be heated to drive off condensed products from the charcoal. The trap may be heated by flowing warm gas, such as air, through the air inlet/outlet tube. In a particularly preferred embodiment, a thin, flexible, electric heating element is inserted in the air inlet/outlet tube to heat the cold trap canister.

Cooling with liquid nitrogen can be problematic. The lines are susceptible to freezing, thus limiting the flow of the liquid. This can cause the cold trap to heat up and evaporate or not condense and trap the gas, leading to lost data. The venting of nitrogen in confined, inhabited spaces is also a concern. Additionally, the liquid nitrogen cooled traps usually use a great amount of liquid nitrogen, making maintaining an adequate supply a problem.

Most cold traps are a single welded assembly. Therefore, the entire cold trap assembly must be treated as radioactive material for disposal, which can be very costly. The design of the present invention reduces the components exposed to radioactivity, thus minimizing the amount of material that must be treated as radioactive waste.

It is an object of the present invention to cool the cold trap with a removable cryogenic cooling device that does not become radioactively contaminated under normal operating circumstances.

It is another object of the present invention to use a cryogenic cooling device, rather than liquid nitrogen, to cool the cold trap.

It is yet another object of the present invention to limit the exposure to radiation to the cold trap, so that the vacuum canister, and removable cryogenic cooling device may be reused.

SUMMARY OF THE INVENTION

The present invention uses a cold trap that is cooled by an off-the-shelf, self-contained cryogenic cooling device, instead of liquid nitrogen. The trap has four major components: (1) a removable cryogenic cooling device (2) a vacuum canister, (3) a cold trap canister filled with activated charcoal, and (4) a cover assembly with welded inlet/outlet tubes and an o-ring seal between the cover assembly and the vacuum canister.

The removable cryogenic cooling device is a closed cooling system capable of keeping the cold trap canister cool enough to condense the hot gas, near liquid nitrogen temperatures, around −150° C. In a particularly preferred embodiment, an integral portable compressor is connected to the cryogenic cooling device with a flexible metal hose. The cryogenic cooling device is removable and is secured to the bellows with standard vacuum fittings. Because the cold trap canister is a sealed assembly, the cryogenic cooling device does not become radioactively contaminated under normal operating conditions, and can be removed and reused for other analyses.

The cover assembly has a flexible vacuum bellows welded to it, to which the cryogenic cooling device is attached using standard vacuum connections. Stainless steel tubes are attached to the cover assembly for purge gas inlet and outlets, a heated air inlet/outlet, a thermocouple, and a vacuum port.

The cold trap canister portion of the invention comprises a cylindrical canister with gas diverters radiating from its inner surface. The canister can be made from any conductive metal that does not react with the process gases and does not affect the seal integrity of the welded tubes. In a particularly preferred embodiment, the canister is made of copper and is filled with activated charcoal. The canister also has inlet and outlet tubes for purge gas flow.

The vacuum canister can be made from any durable material that can withstand a vacuum. In a particularly preferred embodiment, the vacuum canister is a modified stainless steel beaker. A cover assembly is bolted to the vacuum canister with an o-ring seal between the cover assembly and vacuum canister.

DETAILED DESCRIPTION OF THE INVENTION

Figure 1:
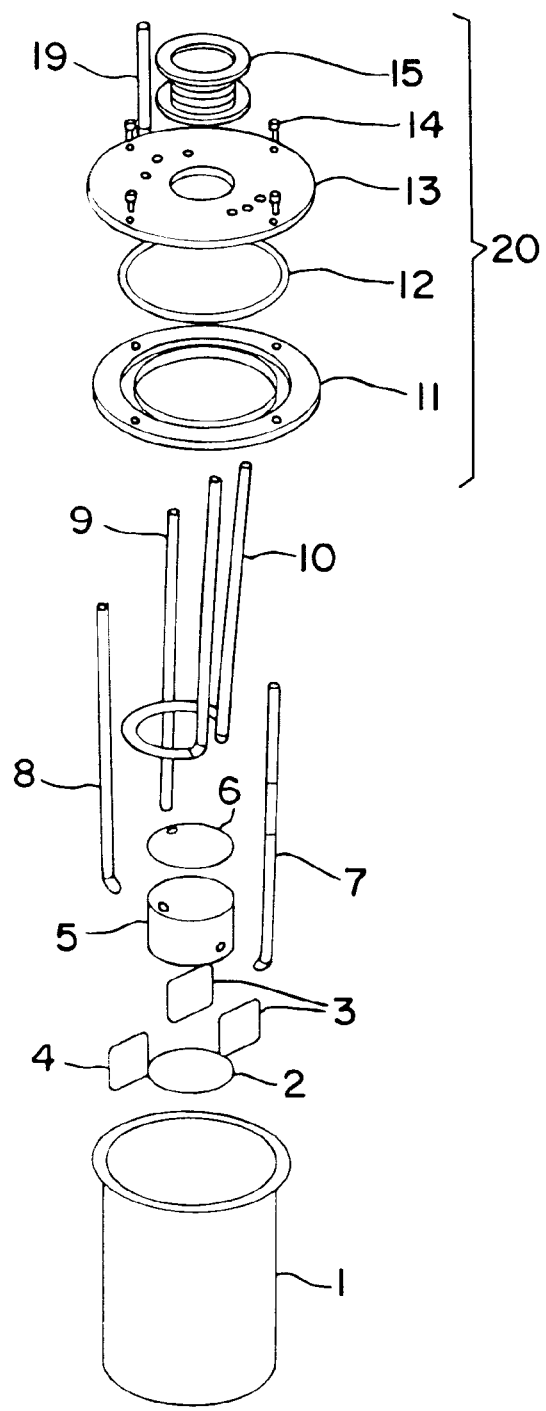
FIG. 1 is a drawing of the vacuum canister, cold trap canister, and cover assembly, showing the relationship of all the components.
Figure 4:
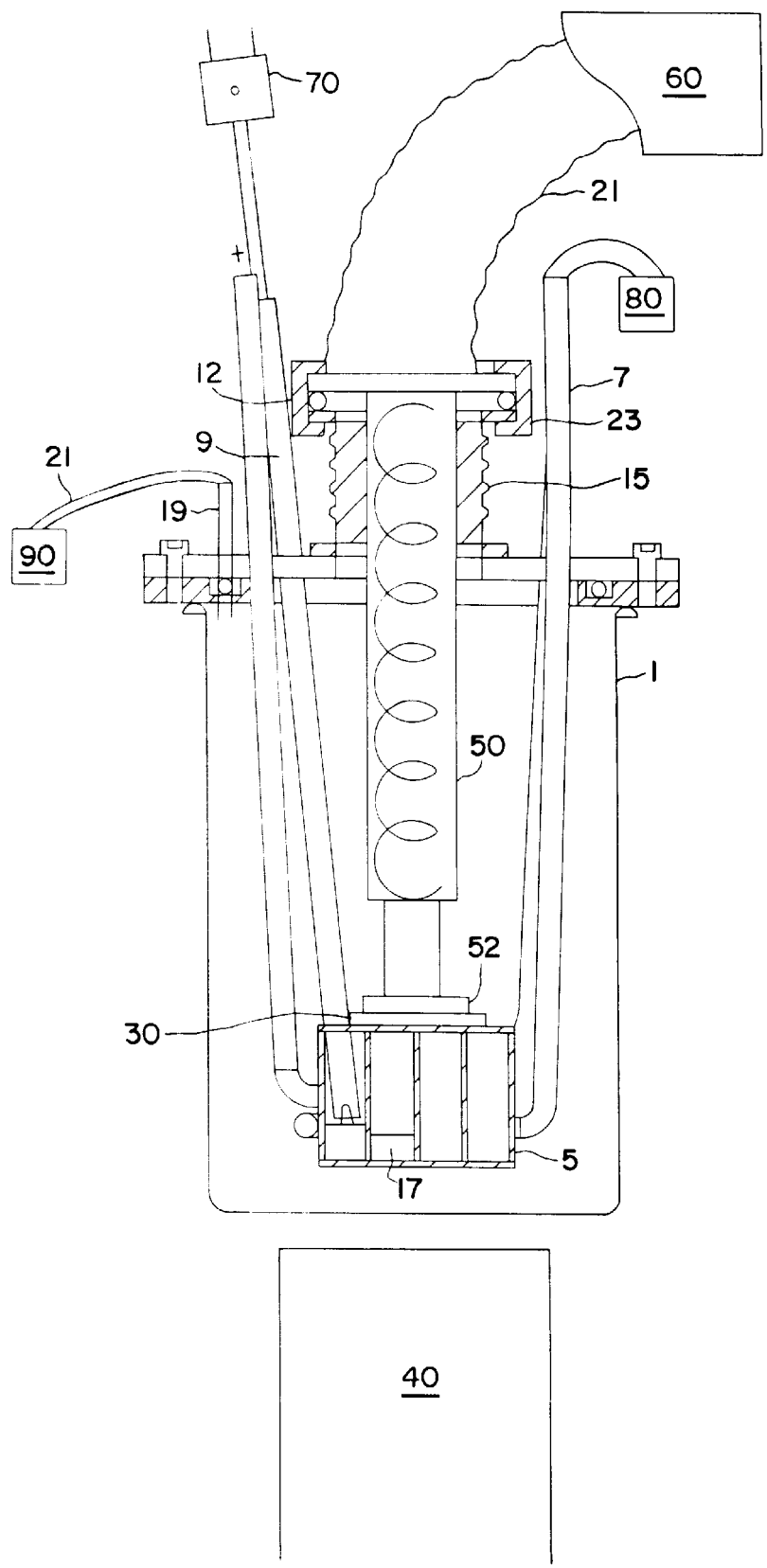
FIG. 4 is a system drawing showing the cryogenic cooling device, radiation detector, compressor, vacuum pump, and thermocouple.

The invention, a cold trap apparatus, collects condensable hot gas products for analysis. The preferred embodiment is adapted to condense, collect, and analyze hot radioactive gases that evolve from annealing fuel at high temperatures, however, the invention could be used to condense, collect, and analyze any hot, condensable gases. A purge gas carries the fission gas products from the furnace 80 and flows through a purge gas inlet tube 7 to a cold trap canister 5 filled with activated charcoal 17. See FIG. 4. The cold trap canister 5 is preferably made of copper and has a plurality of copper cooling gas diverters 3 that are soldered or welded to either the top or bottom cover of the cold trap canister 5 such that they radiate from the inner surface of the cold trap canister 5. See FIGS. 1 and 3. In a particularly preferred embodiment, three cooling gas diverters 3 are used. The cold trap canister 5 and cooling gas diverters 3 provide optimum heat transfer between the charcoal 17 within the cold trap canister 5 and the environment within the vacuum canister 1. The cold trap canister 5 also contains screens 18 at the purge gas inlet 7 and outlet 8 tubes to keep the charcoal 17 from escaping from the cold trap canister 5. See FIG. 3.

Stainless steel tubes, used for purge gas inlet 7 and outlet 8, are welded to opposite sides of the cold trap canister 5. See FIG. 3. The purge gas inlet tube 7 is kept as low as possible to allow for ease of detection by the radiation detector 40 of any fission gas condensation on the cold portion of the purge gas inlet tube 7. In a particularly preferred embodiment, the radiation detector 40 is a sodium iodide radiation detector and is located in close proximity to the bottom of the cold trap canister 5. The cold plate 52 of the cryogenic cooling device 50 makes good operable contact with the malleable metal conductor 30 of the cold trap canister 5 due to the force of the bellows 15 caused by the vacuum in the vacuum canister 1. In a particularly preferred embodiment, the malleable metal conductor 30 is made from indium. During operation, the vacuum inside the vacuum canister 1 provides a force to collapse the bellows 15 and force the cold plate 52 of the cryogenic cooling device 50 into contact with the malleable metal conductor 30 of the cold trap canister 5. This arrangement allows for maximum heat transfer between the cryogenic cooling device 50 and the cold trap canister 5.

Figure 5:
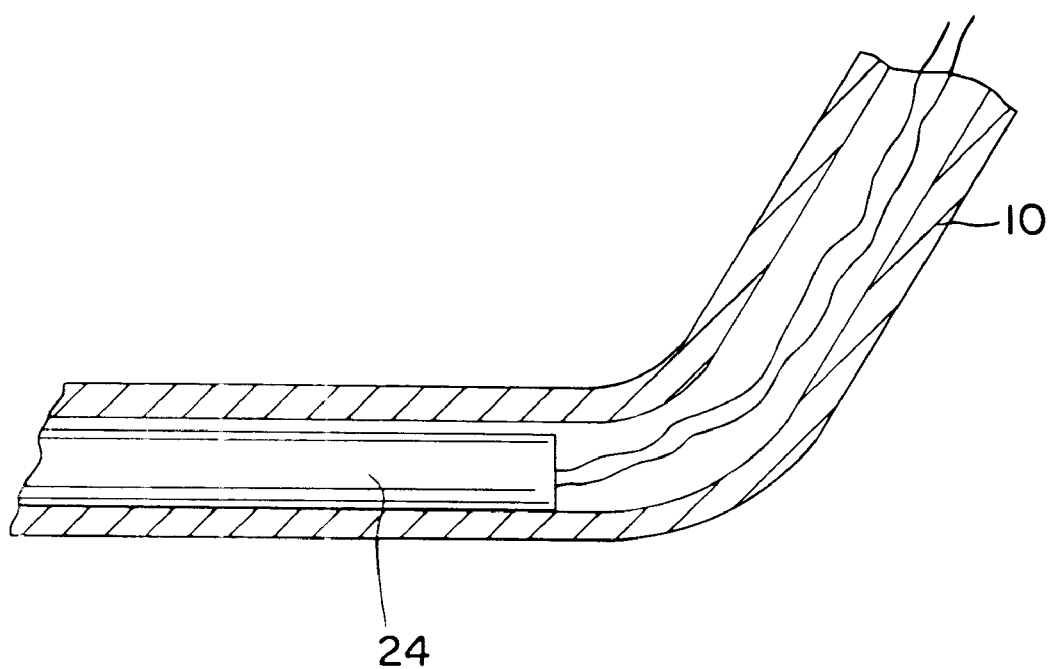
FIG. 5 is a drawing of the internals of the heated air inlet/outlet tube.

A thermocouple tube 9, sealed at the bottom 16, is welded to the cover assembly 20 and is placed near the cold trap canister 5 in the vacuum canister 1. See FIG. 4. The thermocouple tube 9 is open at the top for insertion of a thermocouple 70, which monitors the temperature within the cold trap canister 5. Alternatively, a radioactive source may be inserted into the thermocouple tube 9 to calibrate the radiation detector 40. The heated air inlet/outlet tube 10 is positioned such that a portion of the tube 10 is in contact with the outer surface of the cold trap canister 5, and is welded to the cold trap canister cover 6. See FIG. 1. In a particularly preferred embodiment, the heated air inlet/outlet tube 10 partially encircles the outer surface of the cold trap canister 5. This heated air inlet/outlet tube 10 contains an electric heating element 24 and passes heated air to drive off the condensed gas when the analyses are completed, or to vary the cool down, heat up, or soak temperature by varying the flow of a liquid or gas through the line. See FIG. 5.

The cover assembly 20 contains heated air inlet/outlet tubes 10, purge gas inlet 7 and outlet 8 tubes, a thermocouple tube 9, and the vacuum port 19 all of which are seal welded to the cover 13. The bellows 15 is also welded to the cover 13. The cryogenic cooling device 50 will vacuum seal against the bellows 15 during operation when a vacuum is applied to the vacuum canister 1 using vacuum pump 90. A contact between the cold plate 52 of the cryogenic cooling device 50 and the malleable metal conductor 30 of the cold trap canister 5 is further magnified when vacuum is applied, pulling the cryogenic cooling device downward by collapsing the bellows 15.

In a preferred embodiment, the cryogenic cooling device 50 is a Cryotiger Tigertail available from APD Cryogenics, Inc. The cryogenic cooling device 50 is a self-contained refrigeration system that cools the charcoal cold trap to about −150° C. See FIG. 4. The cryogenic cooling device 50 is attached to a compressor 60. In a particularly preferred embodiment, the cryogenic cooling device 50 is attached to the compressor 60 by flexible steel lines 21. The cryogenic cooling device 50 can be removed from the apparatus by removing a standard vacuum clamp 23. See FIG. 4. Because the radioactive portions of the cold trap apparatus (i.e., the inlet 7 and outlet 8 purge gas tubes and the cold trap canister 5) constitute a sealed system, the cryogenic cooling device 50 should not become contaminated during normal operating conditions, and can be easily removed, reused, or replaced.

Figure 2A:
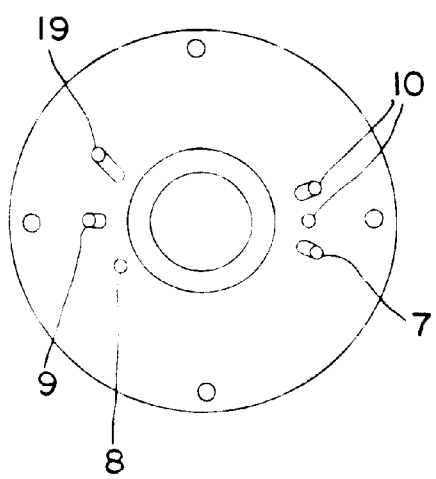
FIG. 2 is an assembly drawing of the vacuum canister, cold trap canister, and cover assembly.
Figure 2B:
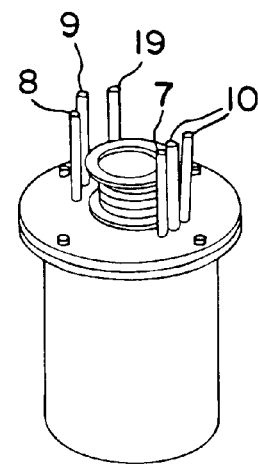
Figure 2C:
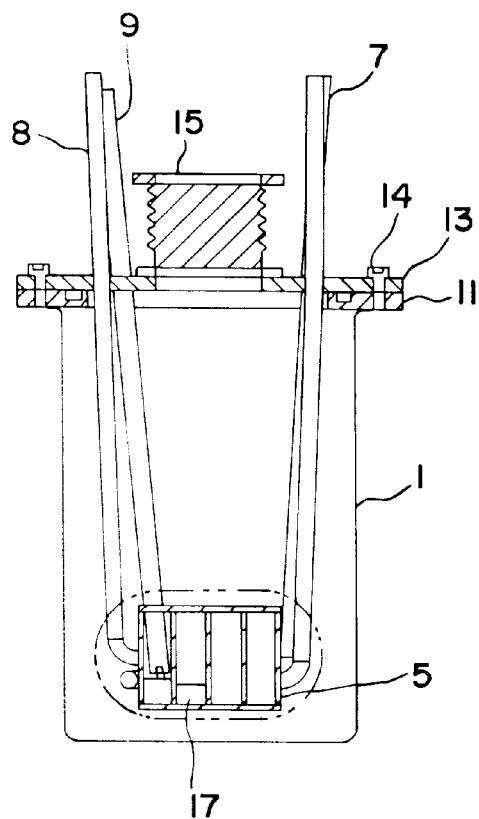
Figure 3A:
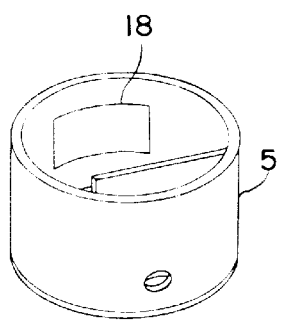
FIG. 3 is a drawing of the internals of the cold trap canister.
Figure 3B:
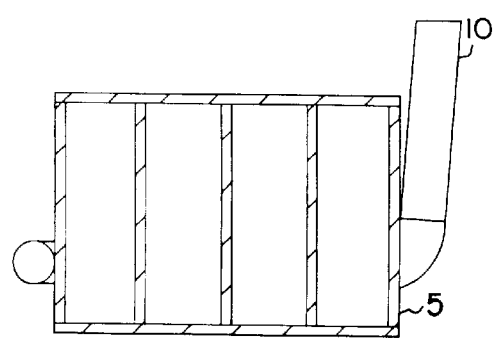
Figure 3C:
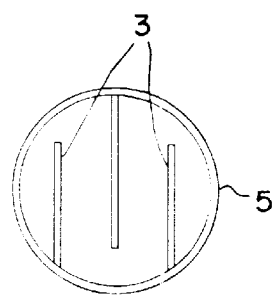
Figure 3D:
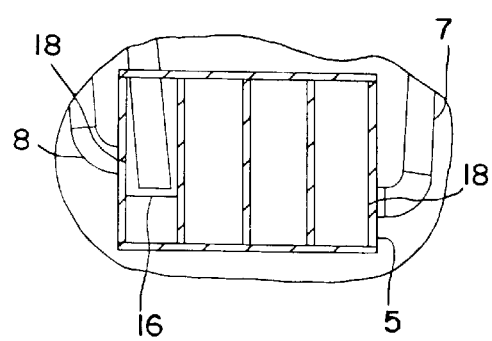

A vacuum canister 1 is sealed to the cover assembly 20 by an o-ring 12 and hold down bolts 14. See FIGS. 1 and 2. The vacuum canister maintains a vacuum and provides insulation around the cold trap canister 5. The vacuum canister 1 is preferably a standard 1200 cc stainless steel beaker. An o-ring 12 and hold down bolt flange 11 are seal welded to the top of the vacuum canister 1, which is bolted to the cover 13 of the cover assembly 20. See FIGS. 1 and 2.

While this invention has been described as having preferred ranges, materials, and designs, it is understood that it is capable of further modifications, uses and adaptations of the invention following in general the principle of the invention, and including such departures from the present disclosure, as those come within the known or customary practice in the art to which the invention pertains and as may be applied to the central features set forth herein, and fall within the scope of the invention and of the appended claims. It is further understood that the present invention is not limited to the claims appended hereto.

What is claimed is:

1. An apparatus for the condensation, collection, and analysis of hot gases comprising
    a. a vacuum canister;
    b. a cold trap canister operably disposed in said vacuum canister;
    c. a cover assembly operably attached to said vacuum canister; and
    d. a removable cryogenic cooling device operably attached to said cold trap canister.

2. The apparatus of claim 1 wherein said vacuum canister is made of stainless steel.

3. The apparatus of claim 2 wherein said vacuum canister is a 1200 cc stainless steel canister.

4. The apparatus of claim 1, wherein said vacuum canister is seal welded to a hold-down bolt flange, said hold-down bolt flange being adapted for an o-ring.

5. The apparatus of claim 4 wherein said hold-down bolt flange contains an o-ring and is bolted to said cover assembly.

6. The apparatus of claim 1 wherein said cold trap canister contains activated charcoal.

7. The apparatus of claim 6 wherein said cold trap canister is composed of copper.

8. The apparatus of claim 7 wherein said cold trap canister comprises a plurality of copper cooling gas diverters that radiate outward from the inner surface of said cold trap canister.

9. The apparatus of claim 1, wherein a radiation detector is in close proximity to said cold trap canister.

10. The apparatus of claim 1, wherein a thermocouple tube is welded onto said cold trap canister.

11. The apparatus of claim 1 wherein said cold trap canister contains a plurality of openings onto which purge gas inlet and outlet tubes are welded.

12. The apparatus of claim 11 wherein said purge gas inlet and outlet tube openings are covered by screens.

13. The apparatus of claim 1 wherein said cover assembly contains a plurality of openings.

14. The apparatus of claim 13 wherein a thermocouple tube, purge gas inlet and outlet tubes, a heated air inlet/outlet tube, a vacuum port, and a bellows are welded to said cover assembly openings.

15. The apparatus of claim 14 wherein said heated air inlet/outlet tube is positioned such that a portion of said heated air inlet/outlet tube is in contact with the outer surface of said cold trap canister.

16. The apparatus of claim 14 wherein said removable cryogenic cooling device is operably attached to said bellows by a vacuum clamp.

17. The apparatus of claim 1 or 16 wherein said removable cryogenic cooling device is a self-contained refrigeration system capable of cooling said cold trap canister to about −150° C.

18. An apparatus for condensing and collecting hot gas comprising a. a stainless steel vacuum canister, b. a removable cryogenic cooling device that is a self-contained refrigeration system capable of cooling a cold trap canister to about −150° C.

c. a copper cold trap canister containing activated charcoal wherein said cold trap canister comprises a plurality of copper cooling gas diverters which radiate outward from the inner surface of said cold trap canister.

d. a cover assembly operably attached to said vacuum canister wherein a thermocouple tube, purge gas tubes, a heated air inlet/outlet tube, a vacuum port, and a bellows are welded to said cover assembly.

* * * * *